United States Patent [19]

Simon et al.

[11] Patent Number: 4,636,568

[45] Date of Patent: Jan. 13, 1987

[54] AMINOETHER COMPOUNDS

[75] Inventors: Myron S. Simon, West Newton; David P. Waller, Lexington, both of Mass.

[73] Assignee: Polaroid Corporation, Cambridge, Mass.

[21] Appl. No.: 644,911

[22] Filed: Aug. 27, 1984

[51] Int. Cl.$^4$ .................... C07D 335/00; C07C 93/08; C07C 93/04

[52] U.S. Cl. ........................................ 549/13; 549/75; 549/373; 549/426; 549/451; 549/491; 556/413; 564/346; 564/360; 564/501; 564/504; 564/508; 558/422

[58] Field of Search ............... 564/346, 360, 501, 504, 564/508; 430/755; 549/13, 75, 373, 426, 451, 491; 556/413; 558/422

[56] References Cited

U.S. PATENT DOCUMENTS 3,238,277  3/1966  Sigan et al. .................... 564/504

OTHER PUBLICATIONS

Meyers, A. I. et al., "Asymetric Synthesis of (+) or (−)-2-Methyloctanal via the Metalloenamines of Chiral Alkoxy Amines", J. Org. Chem., vol. 43, No. 5, 1978.

Primary Examiner—Charles F. Warren
Assistant Examiner—John A. Sopp
Attorney, Agent, or Firm—Gaetano D. Maccarone

[57] ABSTRACT

There are disclosed certain aminoether compounds which are useful as intermediates in the preparation of photographic image dye providing materials. The aminoethers are represented either by the formula

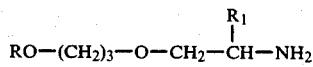

wherein R is hydrogen or an alcohol protecting group and $R_1$ is hydrogen, alkyl or aralkyl such as benzyl or phenethyl; or the formula

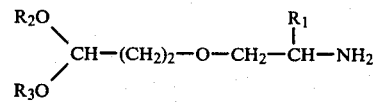

wherein $R_2$ and $R_3$ are alkyl having from 1 to 6 carbon atoms or $R_2$ and $R_3$ together represent the carbon atoms necessary to form, together with the oxygen atoms to which they are bonded and >CH, a five or six member saturated heterocyclic moiety which may include substituted rings and fused rings.

6 Claims, No Drawings

AMINOETHER COMPOUNDS

BACKGROUND OF THE INVENTION

This application is directed to certain aminoether compounds which are useful as intermediates in the synthesis of photographic image dye-providing materials.

U.S. Pat. No. 3,719,489 describes and claims photographic processes employing initially photographically inert compounds which are capable of undergoing cleavage in the presence of the imagewise distribution of silver ions made available during processing of a silver halide emulsion to liberate a reagent, such as a photographically active reagent or a dye in an imagewise distribution corresponding to that of said silver ions. In one embodiment disclosed therein, color images are produced by using as the photographically inert compounds, color providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development to liberate a more mobile and diffusible color-providing moiety in an imagewise distribution corresponding to the imagewise distribution of said ions and/or said complex. The subsequent formation of a color image is the result of the differential in diffusibility between the parent compound and liberated color-providing moiety whereby the imagewise distribution of the more diffusible color-providing moiety released in the undeveloped and partially developed areas is free to transfer.

Copending application Ser. No. 644,915 filed on even date herewith now U.S. Pat. No. 4,535,051, discloses photographic processes for forming a dye image from a substantially colorless precursor which comprises a dye having at least one acylated amino group and which also includes a moiety containing a thiazolidin-2-yl group which upon silver-assisted cleavage initiates a reaction sequence leading to the formation of the image dye. The present application is directed to certain aminoether compounds which are useful as intermediates in the preparation of image dye-providing materials suitable for use in such photographic processes.

SUMMARY OF THE INVENTION

It is therefore an object of the invention to provide novel aminoether compounds.

It is another object to provide such compounds which include an alcohol or a protected alcohol group which will act as a masked aldehyde group, or an aldehyde group protected as an acetal.

BRIEF SUMMARY OF THE INVENTION

These and other objects and advantages are accomplished in accordance with the invention by providing aminoether compounds which are represented either by the formula $$RO-(CH_2)_3-O-CH_2-\underset{R_1}{\overset{|}{C}H}-NH_2 \quad (I)$$

wherein R is hydrogen or an alcohol protecting group and $R_1$ is hydrogen, alkyl, preferably having from 1 to 6 carbon atoms or aralkyl such as benzyl or phenethyl; or the formula

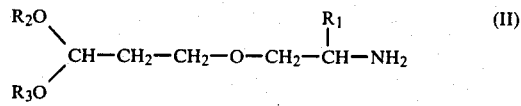

wherein $R_2$ and $R_3$ are alkyl, preferably having from 1 to 6 carbon atoms or $R_2$ and $R_3$ together represent the carbon atoms necessary to form, together with the oxygen atoms to which they are bonded and $>CH-$, a five or six member saturated heterocyclic moiety including substituted rings and fused rings.

The heterocyclic moieties formed by $R_2$ and $R_3$ together include a single heterocyclic ring such as

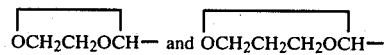

and fused rings such as

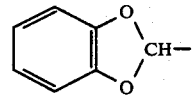

as well as single or fused rings which are substituted.

The alcohol protecting group in Formula I may be any group which allows the protected alcohol to be converted to an aldehyde group without cleaving the other ether group in the compound. Many suitable alcohol protecting groups are known in the art. For a description of alcohol protecting groups see Protective Groups in Organic Synthesis, T. W. Greene, John Wiley and Sons, New York, particularly pages 10 and 11. Typical suitable alcohol protecting groups which can be incorporated in the aminoethers of the invention include

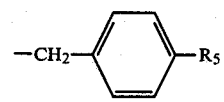

where $R_5$ can be hydrogen, $-O-CH_3$, $-NO_2$, halogen or $-CN$;

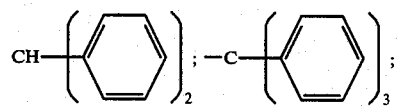

$-CH_2-CH=CH_2$; $-CH_2-R_4-CH_3$ where $R_4$ is $-O-$ or $-S-$;

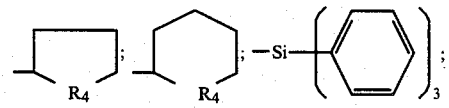

$-Si-C-(CH_3)_3$; and the like.

DESCRIPTION OF THE PREFERRED EMBODIMENTS

The compounds of the invention may be prepared by reactions which are known in the art and these will be readily apparent particularly in view of the specific examples presented herein. Generally, the aminoethers within Formula I can be prepared by reacting 1,3-propanediol with a compound which will provide an alcohol protecting group, e.g., benzyl chloride, to protect one of the alcohol groups, converting the unprotected alcohol group to a methane sulfonate group such as by reaction with methane sulfonyl chloride and reacting the methane sulfonate with an amino alcohol, such as alaninol, to give the desired aminoether. The compounds within Formula II can be prepared by reacting the appropriate alcohol, for example, a 3-hydroxypropionaldehyde acetal, with an allyl halide, e.g., allyl bromide in the presence of NaH to form an acetal alkyl allyl ether, converting the double bond to an azide and reducing the azide to give the desired aminoether.

The invention will now be described further in detail with respect to specific preferred embodiments by way of examples, it being understood that these are intended to be illustrative only and the invention is not limited to the materials, procedures, process parameters, etc. which are recited therein.

EXAMPLE I

Benzyl chloride (104 g, 1.0 m) was added dropwise to a solution of KOH (112 g, 2.0 m) in a mixture of 100 ml of xylene and 304 g of 1,3-propanediol at 50° C.–60° C. The solution was then heated at 100° C. for 2 hours. Water (400 ml) was added to the cooled solution and the mixture was extracted twice with 600 ml of methylene chloride. The combined methylene chloride extracts were washed three times with 400 ml of water, dried over $MgSO_4$, filtered and evaporated to a yellow oil which was distilled under vacuum. The 98° C.–106° C. (1.5 mm) fraction was collected to give 88.7 g of 3-benzyloxypropanol.

To a solution of 3-benzyloxylpropanol (9.9 g, 0.06 m) and methylene chloride (120 ml) deaerated with nitrogen, triethylamine (8.4 ml, 0.06 m) was added with stirring. The solution was cooled to −78° C. and methane sulfonyl chloride (4.62 ml, 0.06 m) was added dropwise. The resultant slurry was warmed to 0° C., stirred for two hours, stored overnight at −20° C., then washed with 100 ml of ice water; 100 ml of ice cold 3% HCl; 100 ml of ice cold 1:1 saturated $NaHCO_3$: water; and water. The methylene chloride layer was dried over $Na_2SO_4$ and evaporated to give a thick straw colored oil. Drying under high vacuum gave 14.79 g of the methane sulfonate,

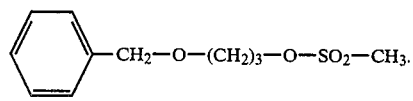

Alaninol (61 ml, 0.0765 m) was added dropwise to a suspension of 50% NaH (3.67 g, 0.0765 m) in 90 ml of tetrahydrofuran and 20 ml of $CH_3CN$. The mixture was refluxed for 45 minutes with stirring and a solution of the methane sulfonate (18.5 g, 0.0758 m) in 15 ml of $CH_3CN$ was added at the reflux temperature. Heating was continued for 2½ hours followed by standing overnight at room temperature. Ethyl ether (200 ml) was added to the solution which was then washed twice with 125 ml of water. The organic solution was then extracted with 150 ml of 5% HCl. The aqueous acid layer was separated, made alkaline with 100 ml of 10% NaOH and extracted twice with 75 ml of ether. The combined ether extracts were dried over $Na_2CO_3$ and Norit, filtered and evaporated to give 7.8 g (48% yield) of the desired aminoether as a yellow oil, b.p. 132°–134° C. (1.75 mm) of the formula

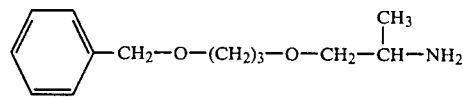

The structure of the compound was determined by a proton NMR spectrum and a mass spectrum. $^1H$ NMR ($CDCL_3$) δ 1 (3H,d), 175 (2H,s), 1.8 (2H,q), 3.2 (3H,m), 3.5 (4H,t), 4.4 (2H,s), 7.2 (5H).

EXAMPLE II 1,3-Propanediol (120 ml, 1.66 m) and dihydropyran (54 ml, 0.59 m) were mixed with vigorous stirring and 10 drops of conc. HCl added with cooling. The reaction mixture was stirred for 3 days. The resulting clear viscous solution was diluted with 350 ml of methylene chloride and washed successively with 150 ml of saturated $NaHCO_3$, 150 ml of water and 10 ml of saturated $NaHCO_3$, and 100 ml of water. The light yellow methylene chloride layer was dried over $Na_2CO_3$, filtered and evaporated to give an oil which was distilled. The desired tetrahydropyranyl alcohol was collected at 123°–124° C.

A solution of the alcohol (10 g, 0.0625 m) in 130 ml of methylene chloroide and 8.72 ml of triethylamine was cooled to −78° C. and 4.85 ml of methane sulfonyl chloride added rapidly. The cold solution was allowed to warm to −20° in a freezer overnight. The solution was washed twice with ice water and once with ice cold 10% $Na_2CO_3$, dried over $Na_2CO_3$, filtered and evaporated to give a viscous oil which was dried under vacuum to give 14 g of the methane sulfonate, a straw colored oil.

Alaninol (5 ml, 0.0627 m) and 50% NaH (3.01 g, 0.0627 m) were combined in 80 ml of tetrahydrofuran and 20 ml of $CH_3CN$ and refluxed for 45 minutes with stirring to form a cream colored suspension. A solution of the methane sulfonate in 15 ml of $CH_3CN$ was added all at once to the refluxing suspension. The reaction mixture became homogeneous and a precipitate developed in about 5 minutes. Refluxing was continued for two hours and the mixture then stirred overnight.

Ether (250 ml) was added to the mixture and the resulting solution was washed with saturated salt solution. The organic solvent layer was evaporated and dried under vacuum to give a crude brown oil. The oil was distilled and the fraction at 98°–113° C. collected to give 4.86 g (38% yield) of the desired product, a colorless liquid of the formula

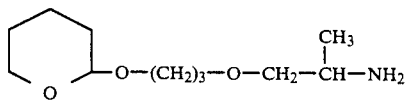

The structure of the product was confirmed by a mass spectrum and ¹H NMR spectrum.

EXAMPLE III

3-Hydroxypropionaldehyde diethyl acetal (3 g, 002 m)

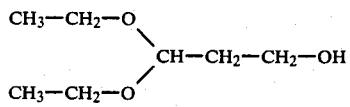

was dissolved in 2 ml of dry dimethylformamide and added dropwise to a stirred suspension of 960 mg of 50% NaH in 8 ml of dry dimethylformamide. The mixture was stirred at 40° C. for 10 minutes until hydrogen evolution slackened. The mixture was then cooled to 0° C. and 1.8 ml of allyl bromide added dropwise with stirring. A white precipitate formed near the end of the addition. Stirring was continued at room temperature for 1 hour.

Ether (50 ml) was added to the mixture and it was then washed four times with 50 ml of 1:1 water and saturated NaHCO₃ and then with saturated salt solution. The ether layer was then dried over Na₂CO₃, filtered and evaporated at below 35° C. to give 3.4 g (90% yield) of crude allyl ether.

A suspension of Hg(OAc)₂ (638 mgs, 2.0 mm) and NaN₃ (200 mg) in 3.5 ml of tetrahydrofuran and 2.5 ml of water was formed. The allyl ether was dissolved in 1.5 ml of tetrahydrofuran and 1 ml of water and the resultant solution added to the suspension which was stirred vigorously at 50° C. The solid dissolved and two layers formed within 2 minutes. Stirring was continued overnight. A 10% NaOH solution (2 ml) followed by a solution of 200 mg of NaBH₄ in 2 ml of 10% NaOH was added. The reaction mixture turned yellow orange upon addition of the base and became black upon addition of the NaBH₄. Ether and water were added and the aqueous layer discarded along with the mercury which sank to the bottom. The ether layer was washed several times with 1:1 water-saturated NaHCO₃ and then with saturated salt solution. The layer was dried over Na₂CO₃.

The crude product was chromatographed on silica gel column with methylene chloride as the eluent to give 127 mg of the pure ether product.

The chromatographically pure ether (4.11 g) was dissolved in 20 ml of anydrous ether and added dropwise with stirring to a suspension of LiAlH₄ (1 g) in 40 ml of ethyl ether under nitrogen at room temperature. The reduction was exothermic and the ether soon began to reflux. Ether (5 ml) was added and the mixture refluxed for 2 hours. The cooled solution was then quenched by the addition of 1 ml of water, 1 ml of 15% NaOH, and 3 ml of water. A granular gray precipitate formed.

The solid was collected by filtration and washed several times with ether. The combined filtrate and washings were dried over Na₂SO₄, decanted and evaporated to give an oil which was stored under nitrogen overnight. The unreacted allyl ether was distilled off at 60°-75° C. (1.2 mm) and the residue collected and dried under vacuum to give 2.05 g of the acetal aminoether having the formula

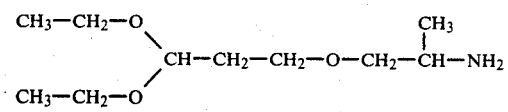

The structure of the compound was confirmed by an IR spectrum and a ¹H NMR spectrum.

Although the invention has been described with respect to specific preferred embodiments, it is not intended to be limited thereto but rather those skilled in the art will recognize that variations and modifications may be made therein which are within the spirit of the invention and the scope of the appended claims.

What is claimed is:

1. A compound represented by the formula

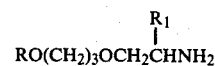

or the formula

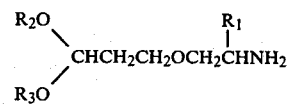

wherein R is

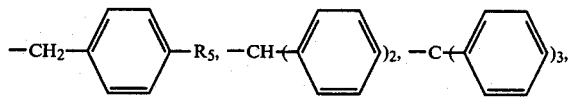

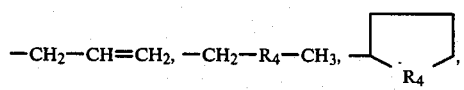

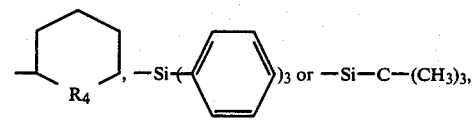

$R_1$ is hydrogen, alkyl having from 1 to 6 carbon atoms, benzyl or phenethyl; $R_2$ and $R_3$ are alkyl having from 1 to 6 carbon atoms; or $R_2$ and $R_3$ together represent the carbon atoms necessary to form, with the oxygen atoms to which they are bonded and >CH—, a five or six member saturated heterocyclic moiety; $R_4$ is —O— or —S—; and $R_5$ is hydrogen, —O—CH₃, —NO₂, halogen or —CN.

2. A compound as defined in claim 1 which is represented by the formula

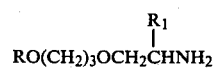

wherein $R_1$ is alkyl having from 1 to 6 carbon atoms.

3. A compound as defined in claim 2 wherein R is

4. A compound as defined in claim 1 which is represented by the formula

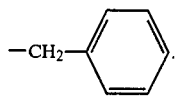

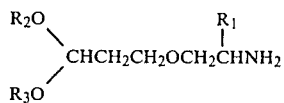

wherein $R_1$ is alkyl having from 1 to 6 carbon atoms.

5. A compound as defined in claim 4 wherein $R_2$ and $R_3$ are alkyl having from 1 to 6 carbon atoms.

6. A compound as defined in claim 4 wherein $R_2$ and $R_3$ together represent the carbon atoms necessary to form, together with the oxygen atoms to which they are bonded and >CH—, a five or six member saturated heterocyclic moiety.

* * * * *